(12) United States Patent
Fountain et al.

(10) Patent No.: US 8,732,864 B2
(45) Date of Patent: May 27, 2014

(54) SAFETY APPARATUS

(75) Inventors: Peter David Fountain, Oakleigh (AU); Brendan Michael Krone, Langwarrin (AU); John Magree, Mitcham (AU)

(73) Assignee: Loud & Clear Safety Pty Ltd, Oakleigh (AU)

( * ) Notice: Subject to any disclaimer, the term of this patent is extended or adjusted under 35 U.S.C. 154(b) by 330 days.

(21) Appl. No.: 13/060,537

(22) PCT Filed: Aug. 19, 2009

(86) PCT No.: PCT/AU2009/001064
§ 371 (c)(1),
(2), (4) Date: May 3, 2011

(87) PCT Pub. No.: WO2010/022440
PCT Pub. Date: Mar. 4, 2010

(65) Prior Publication Data
US 2011/0209273 A1 Sep. 1, 2011

(30) Foreign Application Priority Data

Aug. 25, 2008 (AU) ................................ 2008904382
Aug. 4, 2009 (AU) ................................ 2009903641

(51) Int. Cl.
*A42B 1/06* (2006.01)
(52) U.S. Cl.
USPC .......................................................... 2/209
(58) Field of Classification Search
USPC ........ 2/209, 423, 422, 452; 181/129; 351/158
See application file for complete search history.

(56) References Cited

U.S. PATENT DOCUMENTS

| 1,117,968 | A | * | 11/1914 | De Bobory | ........................ 2/426 |
| 1,768,597 | A | | 7/1930 | Gwathmey, Jr. | |
| 2,413,283 | A | | 12/1946 | Berg | |
| D150,508 | S | | 8/1948 | Mendelsohn | |
| 2,512,508 | A | | 6/1950 | Shepelevich | |
| 2,556,433 | A | | 6/1951 | Mitchell | |
| D176,309 | S | | 12/1955 | Clark | ............................... D57/1 |
| D204,023 | S | | 3/1966 | Potts | ................................. D57/1 |
| 3,335,720 | A | * | 8/1967 | Aileo | ............................ 128/866 |

(Continued)

FOREIGN PATENT DOCUMENTS

| AU | 2009201810 A1 | 5/2009 | ............. A61F 11/14 |
| CN | 201001810 | 1/2008 | ............. A61F 11/14 |

(Continued)

OTHER PUBLICATIONS

European Patent Office, EP09809093.9, European Search Report, Oct. 27, 2011.

(Continued)

*Primary Examiner* — Amber Anderson
(74) *Attorney, Agent, or Firm* — Sunstein Kann Murphy & Timbers LLP (57) ABSTRACT

An ear muff style ear protector device having a body for permitting positioning on a wearer's head, and two ear muff ear protectors connected with the body, so the ear protectors can be operatively held relative to a wearer's ears. At least one ear protector can be adapted to selectively enable the wearer to temporarily reduce the level of sound protection to the respective ear to enable external sounds to be heard more clearly. In an embodiment the body is an eye protector assembly, which is connected to the two ear muff ear protectors.

19 Claims, 10 Drawing Sheets

(56) References Cited

U.S. PATENT DOCUMENTS

| | | | |
|---|---|---|---|
| 3,661,225 A * | 5/1972 | Anderson | 181/175 |
| 3,719,954 A | 3/1973 | Beguin | 2/209 |
| 3,943,574 A * | 3/1976 | Yamaguchi et al. | 2/9 |
| 4,103,359 A * | 8/1978 | Rieppel et al. | 2/8.1 |
| 4,133,053 A | 1/1979 | Lundin | 2/209 |
| 4,393,519 A | 7/1983 | Nicastro | 2/12 |
| 4,602,856 A | 7/1986 | Marks | 351/44 |
| 4,682,374 A | 7/1987 | Geiser | 2/209 |
| 4,802,243 A * | 2/1989 | Griffiths | 2/422 |
| 4,856,089 A * | 8/1989 | Horton | 455/351 |
| D317,167 S | 5/1991 | Downey | D16/102 |
| 5,046,192 A * | 9/1991 | Ryder | 2/12 |
| 5,092,667 A | 3/1992 | Bagley | 351/156 |
| 5,133,596 A * | 7/1992 | Korny et al. | 351/158 |
| 5,179,736 A * | 1/1993 | Scanlon | 2/209 |
| 5,201,856 A * | 4/1993 | Edwards | 2/209 |
| 5,278,999 A | 1/1994 | Brown | 2/209 |
| 5,289,592 A | 3/1994 | Paivarinta | 2/431 |
| D352,300 S * | 11/1994 | Gales | D16/309 |
| 5,421,037 A | 6/1995 | Schulze | 2/452 |
| 5,546,610 A * | 8/1996 | Herzig et al. | 2/422 |
| D380,872 S | 7/1997 | Wickland | D29/109 |
| 5,713,078 A * | 2/1998 | DeAngelis | 2/209 |
| 5,718,002 A | 2/1998 | Pavlak | 2/423 |
| 5,724,119 A | 3/1998 | Leight | 351/158 |
| 5,813,056 A * | 9/1998 | Ambrose | 2/452 |
| D404,174 S * | 1/1999 | Childs et al. | D29/112 |
| 5,930,842 A * | 8/1999 | Burruss | 2/452 |
| 5,943,703 A * | 8/1999 | Avila, Jr. | 2/209 |
| 6,065,157 A * | 5/2000 | Felman | 2/209 |
| D428,620 S | 7/2000 | Maturaporn | D16/314 |
| D439,597 S | 3/2001 | Marcum | D16/312 |
| 6,511,177 B1 * | 1/2003 | Hall et al. | 351/158 |
| D485,854 S | 1/2004 | Thomason | D16/301 |
| 6,728,974 B2 * | 5/2004 | Wadsworth | 2/456 |
| 6,826,287 B2 * | 11/2004 | Myers | 381/373 |
| 7,020,901 B2 * | 4/2006 | Brhel | 2/209 |
| 7,020,903 B2 * | 4/2006 | Artzberger | 2/431 |
| 7,058,992 B1 * | 6/2006 | Ogonowsky | 2/448 |
| D565,082 S | 3/2008 | McClure et al. | D16/309 |
| 2005/0015852 A1 | 1/2005 | Brhel | 2/209 |
| 2006/0015989 A1 | 1/2006 | Faussett et al. | 2/423 |

FOREIGN PATENT DOCUMENTS

| | | | |
|---|---|---|---|
| CN | 201001810 Y | 1/2008 | A61F 11/14 |
| DE | 3821536 A1 | 6/1988 | A61F 9/02 |
| DE | 3821536 | 2/1990 | A61F 9/02 |
| EP | 0353930 | 2/1990 | A61F 9/02 |
| GB | 2209923 | 6/1989 | A61F 9/02 |
| JP | 58-61421 | 4/1983 | A42B 1/24 |
| JP | 59-22418 | 2/1984 | G02C 11/00 |
| JP | 06-017303 | 1/1994 | A42B 3/28 |
| JP | 2006-336116 | 12/2006 | A42B 3/16 |
| JP | 2008-118401 | 5/2008 | H04R 1/10 |
| WO | WO 9807062 | 2/1998 | G02C 11/06 |
| WO | WO 2005/051255 | 6/2005 | A61F 11/14 |
| WO | WO 2008/004274 | 1/2008 | H04R 1/00 |

OTHER PUBLICATIONS

Australian Patent Office, International Preliminary Report on Patentability dated Dec. 6, 2010, PCT/AU2009/001064.

* cited by examiner

SAFETY APPARATUS

FIELD OF THE INVENTION

The field of the invention is safety equipment, in particular wearable safety equipment for protecting a wearer's sight and hearing.

BACKGROUND OF THE INVENTION

Eye protection safety equipment such as safety goggles or visors are known. Such devices provide a barrier in front of the wearer's eye's for protection against flying particles or liquid splashes. Typically the barrier will be transparent or semi-transparent to enable the wearer to see through the barrier. Known hearing protection safety equipment includes ear muffs or ear plugs which are worn to dampen or muffle sounds to minimise hearing damage which may occur from being exposed to a noisy environment.

In some workplaces it is mandatory to wear safety equipment such as eye protection, ear protection, and head protection. It is therefore desirable for such safety equipment to be practical and comfortable. There is a need for safety equipment design improvement.

SUMMARY OF THE INVENTION

According to one aspect of the present invention there is provided an ear muff style ear protector device having a body for permitting positioning on a wearer's head, and two ear muff ear protectors connected with the body, so the ear protectors can be operatively held relative to a wearer's ears so that one ear protector can cover one ear and the other ear protector can cover the other ear wherein at least one ear protector is adapted to selectively enable the wearer to temporarily reduce the level of sound protection to the respective ear to enable external sounds to be heard more clearly.

In an embodiment of the ear muff style ear protector device the body is an eye protector assembly, which is connected to the two ear muff ear protectors so that the body can be moved between a first position where the body rests on the wearer's face to provide protection to the wearer's eyes and one or more alternative positions where the body rests in a position where protection is not provided to the wearer's eyes while the ear protectors can be operatively held relative to a wearer's ears so that one ear protector can cover one ear and the other ear protector can cover the other ear.

In one embodiment each ear protector can be connected with the body by a swing coupling such that an ear protector can be swung from about the swing coupling to crank the ear protector so that the wearer's ear is no longer covered whilst leaving the body positioned on the wearer's head.

In an embodiment the direction of swinging is fore/aft of the wearer's head along the side of the wearer's head.

In an alternative embodiment the direction of swinging is laterally outwardly/inwardly of the wearer's head.

Each swing coupling can have an axis of swing rotation positioned in an upper region of an ear protector.

In another embodiment of ear muff style of ear protector device at least one ear protector is provided with an aperture in a portion of the ear protector wherein the aperture can be selectively opened by the wearer to temporarily reduce the level of sound protection provided from the level of sound protection provided while the aperture is closed.

In some embodiments the aperture is normally closed.

An actuator can be provided which is operable by the wearer to open the aperture when actuated.

According to another aspect of the present invention there is provided a combined ear and eye protection apparatus comprising:

an eye protector adapted to form a barrier for protecting a wearer's eyes;

two ear muff style ear protectors each having a mounting located toward an upper edge of the ear protector for attachment to an arm; and two arms, each arm attached at one end to one side of the eye protector and the other attached to an ear protector mounting, wherein the assembly of the arms and eye protector is resiliently formed such that, when worn, the resilience of the assembly urges the arms and respective ear protectors inwardly to grip the wearer's head and support the apparatus in place when worn.

At least one ear protector can be adapted to selectively enable the wearer to temporarily reduce the level of sound protection to the respective ear to enable external sounds to be heard more clearly.

The at least one ear protector may be provided with an aperture in a portion of the ear protector wherein the aperture can be selectively opened by the wearer to temporarily reduce the level of sound protection provided from the level of sound protection provided while the aperture is closed.

The aperture may be normally closed. An actuator can be provided which is operable by the wearer to open the aperture when actuated.

In an embodiment of the ear and eye protection apparatus each arm can be adapted to enable the position of the ear protector attachment to be moved relative to the eye protector. For example the ear protector may be moveable along a portion of the arm. For example, each arm can have a slider for enabling the position of the ear protector attachment to be moved along a portion of the arm. Alternatively the arm may comprise two portions adjustable relative to each other to enable the overall length of the arm to be altered In an embodiment the slider is a slot in which a portion of the ear protector mounting is retained while allowing the portion of the mounting to be slid along the slot.

In an embodiment of the eye and ear protection apparatus each ear protector mounting can be adapted to enable the ear protector to rotate about more than one axis relative to the arm.

In an embodiment the mounting is a ball and socket type joint, comprising a socket formed in the ear protector and a mounting member having a ball portion adapted to be retained in the socket and an arm attachment portion adapted to engage with the arm to attach the ear protector to the arm.

In some embodiments of the ear and eye protection apparatus the arm and eye protector assembly includes a tensioning member adapted to provide sufficient resilient force to maintain grip on the wearer's head and support the apparatus in place when worn.

In some embodiments of the ear and eye protection apparatus the materials from which the arms and eye protector are formed provide sufficient resilient force through the arm and eye protector assembly to maintain grip on the wearer's head and support the apparatus in place when worn.

Each ear protector can comprise an inner sound insulating portion adapted to rest against and substantially or entirely cover the outer ear of a wearer; and an outer shell made of rigid material and attached to the inner insulating portion, wherein the mounting for connection to the arm is attached to the outer shell of the ear protector.

In some embodiments the outer shell has a removable portion adapted to be selectively removed and replaced whereby when removed an aperture is formed in the outer shell.

The removable portion can be utilised to enable sound insulating qualities of the ear protector to be adjusted by adding or removing additional sound insulating material via the aperture in the outer shell.

The removable portion of the outer shell can be replaceable with an alternative removable portion.

In some embodiment the alternative removable portion caries an active element for installation in the ear protector. In some embodiments the active element is an electronic communication device. For example, the active element can be a wireless hands free unit for a mobile phone.

Another aspect of the invention provides an alternative removable portion of an outer shell of an ear protector as described above.

In an embodiment of the ear and eye protection apparatus the arms are attached to the eye protection portion using hinges.

According to another embodiment of the present invention there is provided an ear muff style ear protector including an aperture in a portion of the ear protector wherein the aperture can be selectively opened by the wearer to temporarily reduce the level of sound protection provided from the level of sound protection provided while the aperture is closed. The aperture may be normally closed. An actuator can be provided which is operable by the wearer to open the aperture when actuated.

BRIEF DESCRIPTION OF THE DRAWINGS

An embodiment, incorporating all aspects of the invention, will now be described by way of example only with reference to the accompanying drawings in which.

DETAILED DESCRIPTION

FIGS. 1 to 6 illustrate a combined ear and eye protection apparatus 100 having an eye protector 110, adapted to form a barrier for protecting a wearer's eyes, and two ear muff style ear protectors 120, 125. Two arms 130, 135 are each connected to one side of the eye protector 110 and an ear protector 120, 125 is connected to each arm 130, 135 respectively using a mounting 150, 155 located towards an upper edge of the ear protector. The assembly of the arms 130, 135 and eye protector is resiliently formed such that, when worn, the resilience of the assembly urges the arms and respective ear protectors 120, 125 inwardly to grip the wearer's head 105 and support the apparatus 100 in place when worn. The resilience of the assembly provides sufficient force to hold the eye and ear protection apparatus in place on a wearer's head without the need for a supporting headband.

It should be appreciated that an advantage of this arrangement is that the safety apparatus may be easily worn and interference with any headwear is minimised. This enables a person to wear the ear and eye protection apparatus with different forms of protective headwear depending on the working environment. For example, the eye and ear protection may be worn with protective headwear such as a hard hat on a construction site, a cap or beanie in a workshop, and sun hat while mowing lawns.

Figure 1:
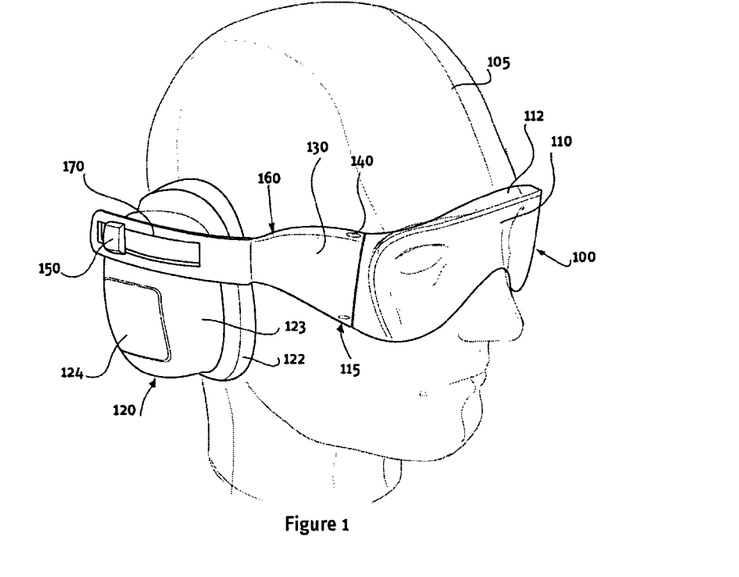
FIG. 1 is an isometric view showing an exemplary embodiment of a combined ear and eye protection apparatus being worn by a person.
Figure 2:
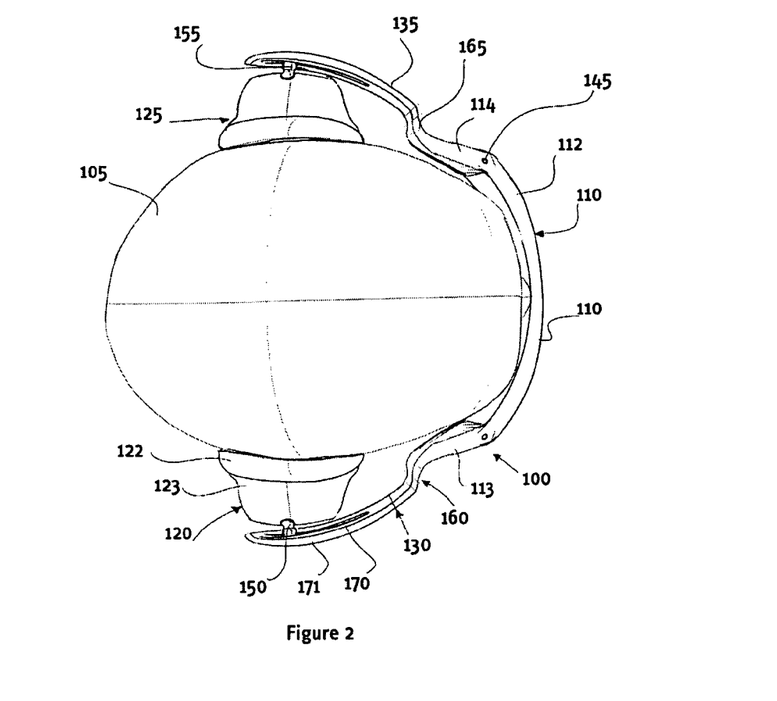
FIG. 2 is a top view of a person wearing the combined ear and eye protection apparatus of FIG. 1.

In the example shown in FIG. 1 the eye protector has a lens or visor adapted to rest on the bridge of a wearer's nose and provide a barrier across the front of their eyes. The visor is transparent or semi-transparent to enable the person to see through the visor to work while the visor acts as a barrier to prevent debris directed towards the wearer's eyes. The eye protector may also have flanged edges extending from the visor toward the persons face to offer protection from debris which may be encountered from other directions, is for example, sideways, above or below. For example as illustrated in FIG. 1 the visor 110 has a brow flange 112 along the top of the visor. Side flanges may also be provided extending rearward from each side of the visor toward the wearer's temples. Alternatively the visor may be curved to provide side and frontal barrier protection.

In some embodiments the arms 130, 135 are shaped to provide a protective barrier to the side of the wearer's eyes. For example, the arms may replace or complement a side flange or curved visor to provide side protection. In the embodiment illustrated in FIGS. 1 and 3 the arm has a first section 113 which provides a side barrier for protecting the wearer's eyes. This first arm section 113 sits proximate the wearer's head to minimise the gap between the wearer's head and the safety apparatus through which debris may penetrate and get into the wearer's eyes. The arm then has a second section 160 where the arm extends outwardly to provide space to accommodate the ear protector 120 against wearer's head 105. A third section 171 extends rearward and the ear protector 120 is attached to this rearward section. In the embodiment illustrated in FIG. 2 the second section provides a curved transition between the first and third sections of the arm. Alternatively, the second section could form an angled or stepped transition between the first and third portions.

In an alternative embodiment the arm may be substantially straight or slightly curved and angled outward to accommodate the ear protector without a distinct transition between the portion attaching to the visor and the portion attaching to the ear protector. In this embodiment the arm may be provided with flanges extending from the arm toward the wearer's head to provide additional side protection as the gap between the wearer's head and the arm may be greater than in the embodiment illustrated in FIG. 2.

The mounting 150 for the ear protector 120 is adapted to attach the ear protector to the arm 130 in a manner which allows the rotation of the ear protector 120 relative to the arm 130. This rotational movement enables the eye protector to be move to or away from a position where the wearer's eyes are protected without needing to move the ear protectors. Two alternative rotational mounting embodiments having different ranges of flexibility are illustrated. The first embodiment, illustrated in FIGS. 1 to 9b, enables ear protectors to be moved away from the wearer's ears. The second embodiment, illustrated in FIGS. 12 to 15b, limits the movement of the ear protectors relative to the wearer's ears. Many further embodiments are also envisaged within the scope of the present invention.

Figure 3:
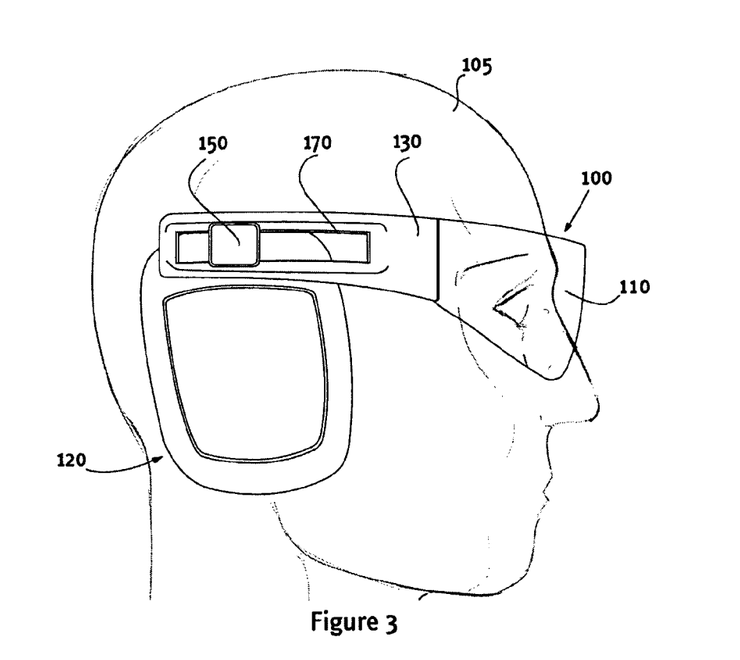
FIG. 3 is a side view of a person wearing the combined ear and eye protection apparatus of FIG. 1.
Figure 4:
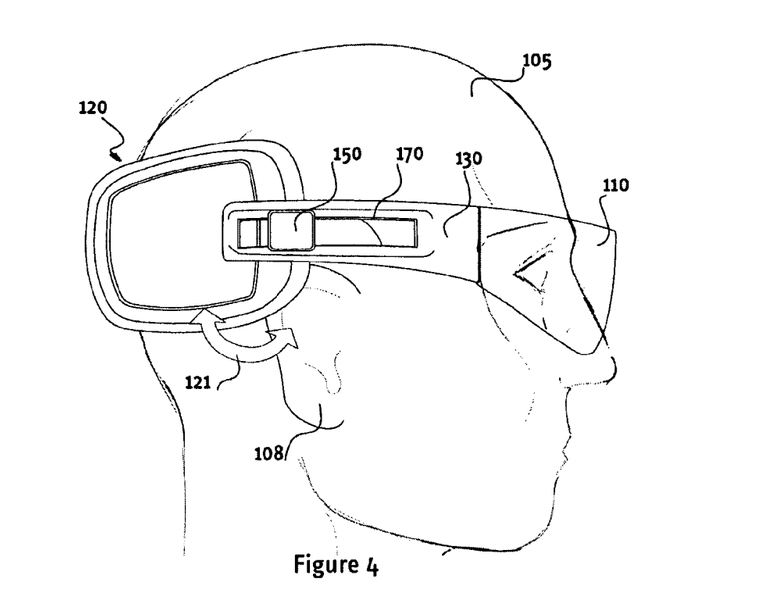
FIG. 4 is a side view of a person wearing the ear and eye protection apparatus of FIG. 1 illustrating an ear protector moved to expose an ear.

A first embodiment of an ear and eye protection apparatus is illustrated being worn by a person in FIGS. 1 to 6. The rotational attachment of the ear protector 120 to the arm 130 illustrated in FIGS. 1 to 6 also enables the ear protector 120 to be moved to expose or cover a wearer's ear independently of the eye protector 110 or other ear protector 125. An example of the movement of the ear protector 120 is illustrated in FIGS. 3 and 4. FIG. 3 illustrates the ear protector 120 in a protective position over the wearer's ear. FIG. 4 illustrates the ear protector 120 moved to expose the wearer's ear 108 for normal hearing, for example to hold a conversation with another person or use a mobile phone. The rotational mounting 150 of the ear protector 120 to the arm 130 and the position of the mounting toward the upper edge of the ear protector 120 enable the ear protector 120 to be rotated 121 away from the wearer's ear 108 without disturbing the eye protector 110. Further each ear protector can be moved independently of the other ear protector. For example, to answer a mobile phone the wearer can simply rotate one ear protector away from their ear and use the phone while leaving the other ear protector and eye protector in place.

The position of the mounting 150 in the upper portion of the ear protector 120 enables the ear protector to swing away from the wearer's ear 108. Although the illustrated embodiment shows the mounting positioned in approximately the middle of the top edge of the ear protector, the position may be varied. The mounting need not be located at the edge of the ear protector, for example locating the mounting anywhere in the upper third of the ear protector can enable the ear protector to effectively rotate away to expose the ear. The exact position of the mounting may be varied depending on the shape of the ear protector or based on other accessories which may be worn in conjunction with the device, such as headwear or face masks. For example the mounting may be located in the rear top corner of the ear protector, such that rotation of the ear protector away from the ear causes minimal disruption to any headwear, for example hard hats or broad brimmed hats. Although in the embodiment illustrated the ear protector rotates rearward to expose the ear, embodiments where the ear protector may be rotated forward are also envisaged.

Each arm can also be adapted to enable the attachment position of the ear protector to be moved along a portion of the arm. In the embodiment illustrated the arm 130 is provided with a slot 170 in which a portion of the mounting 150 is retained. The slot 170 acts as a slider, enabling the attachment point of the ear protector 120 to be adjusted along the length of the slot. This adjustability enables the relative positions of the ear protectors and eye protector to be adjusted to suit the wearer's face.

Figure 5:
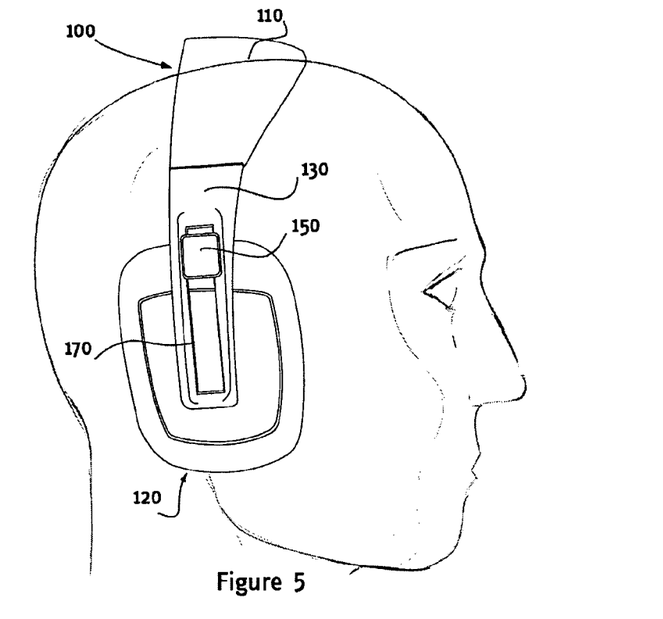
FIG. 5 is a side view of a person wearing the ear and eye protection apparatus of FIG. 1 illustrating the eye protector raised.
Figure 6:
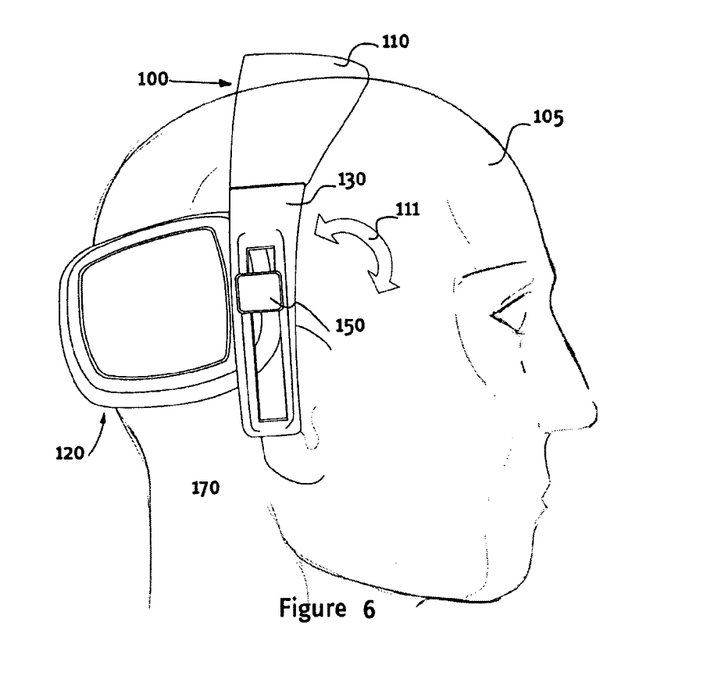
FIG. 6 is a side view of a person wearing the ear and eye protection apparatus similar to that in FIG. 1 illustrating the eye protector raised as well as the ear protector moved to expose an ear.

Further, the ability to change the relative ear protector and eye protector positions enables the wearer to remove the eye protector without disturbing the ear protectors, by lifting the visor which can then rest comfortably on the wearer's head as illustrated in FIGS. 5 and 6. As can be seen in FIG. 5 the visor 110 can be rotated 111 upward and rested on the wearer's head 105. The slot 170 enables the arms 130 to be moved forward, whereby the mounting 150 slides in the slot 170 without disturbing the ear protectors 120, so the visor 110 clears the wearer's forehead as it is lifted. The arms 130 can then be slid downward and the mounting 150 slides in the slot 170 to enable the visor 110 to rest on top of the wearer's head. As can be observed from FIGS. 5 and 6, the relative distance between the visor 110 and the ear protector 120 is closer when the visor rests on the top of the wearer's head than when the visor rests on the bridge of the wearer's nose. Thus, as illustrated in FIG. 6, the eye protection can be moved without disturbing the ear protection. Embodiments may also provide arms with a slot long enough to enable the visor to be moved downward to rest under the wearer's chin, for example to enable the eye protection to be removed without disturbing any headwear.

It should be appreciated from FIG. 5 that both eye and ear protectors can be moved from their respective protective positions without needing to remove the entire eye and ear safety apparatus from the wearer's head. This can be convenient for the wearer. This can also be advantageous on worksites by reducing the likelihood of the eye and ear safety apparatus being misplaced or forgotten.

The embodiment illustrated provides a slider in the form of a slot in which a portion of the ear protector mounting is retained, while allowing the portion of the mounting to be slid along the slot. However, alternative slider arrangements are contemplated. For example, a slider may comprise a rail on which a portion of the ear protector mounting is slidingly engaged.

The resilience of the eye protector and arms assembly causes force to be applied to urge the ear protectors inward to grip the wearer's head. This force may also cause sufficient friction in the slider to inhibit spontaneous relative movement between the arm and mounting, for example, preventing the visor sliding forward when the wearer leans forward, while still enabling the wearer to manually adjust the relative positions of the ear protectors and visor. materials of the slider arrangement may be chosen for appropriate frictional engagement. Alternatively the slider arrangement may have a physical structure to inhibit spontaneous movement. For example, a series of ridges may be formed along an edge of the slot or opposing ridges on each of the mating faces to engage with the mounting to increase the resistance of the visor to sliding while the visor is in position on the bridge of the wearer's nose, while allowing the mounting to slide in the slot when manually moved.

Figure 7:
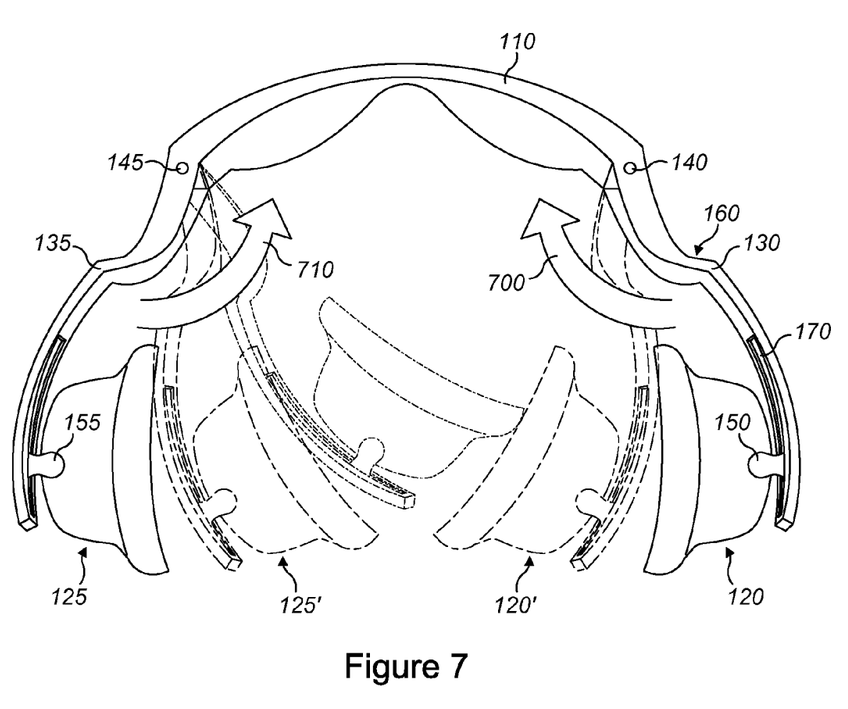
FIG. 7 illustrates an embodiment of a combined ear and eye protection apparatus which is foldable for storage.
Figure 8:
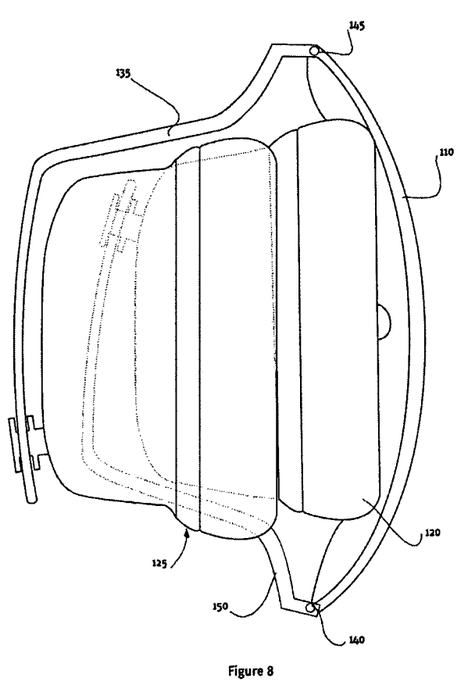
FIG. 8 illustrates the combined ear and eye protection apparatus of FIG. 7 in a folded position.

Embodiments of the ear and eye protector apparatus can have hinged arms to enable the apparatus to be folded for storage. As illustrated in FIGS. 7 and 8 the arms 130, 135 can be attached to the eye protection portion 110 using hinges 140, 145. The hinges 140, 145 enable the arms to be folded inwards 700, 710. The ear protectors 120, 125 can be rotated slightly to enable the apparatus to be folded as illustrated in FIG. 8. In the folded position as illustrated in FIG. 8 it should be appreciated that the ear protectors 120, 125 are somewhat nestled within the visor 110. The visor provides some protection, in the folded position, to reduce the amount of dust, dirt, debris or other contaminates which may get into the ear muffs when they are not being worn, compared to an apparatus which cannot be folded or is not folded so the ear muffs will be exposed to debris when not being worn. Hygiene problems can occur due to accumulation of grime in ear muffs. In an embodiment where the arms are hinged to enable the ear muffs 120, 125 to be folded and shielded from at least some debris by the visor 110 the accumulation of debris in the ear muffs can be reduced. Being able to fold the eye and ear protector apparatus is also advantageous for convenient storage. Further, in the folded position the eye and ear protection apparatus can be conveniently carried hooked onto a belt or strap. It should be appreciated that convenient storage and carrying of the eye and ear protection apparatus can contribute to the willingness of a worker to carry the apparatus with them, ready for use, if necessary, and hence encourage them to always have ear and eye protection on hand.

Figures 9A, 9B:
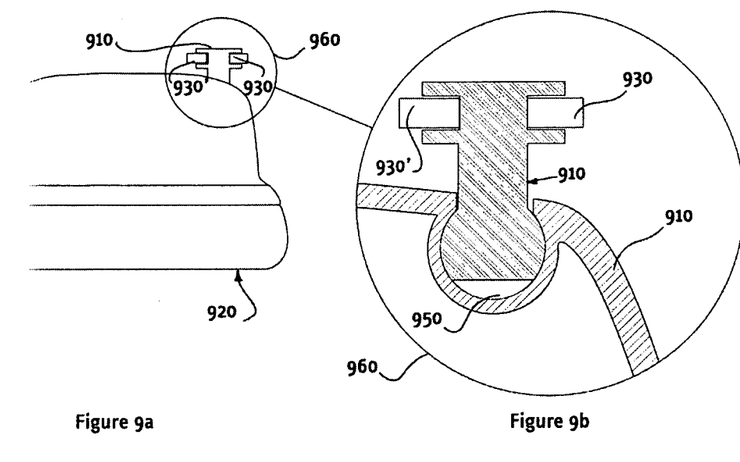
FIGS. 9a and 9b illustrate an embodiment of a mounting joint used for attaching an ear protector to an arm of the combined ear and eye protection apparatus.

The ear protector mounting 150 can be adapted to enable the ear protector to rotate about more than one axis relative to the arm. An example of an embodiment of an ear protector mounting is illustrated in FIGS. 9a and 9b. FIG. 9a illustrates an ear protector 120 having a mounting 960 connecting the ear protector 120 to an arm. A cross section of the mounting assembly 960 is illustrated in detail in FIG. 9b. The mounting 960 of the illustrated example is a ball and socket type joint. The mounting 960 comprises a socket 950 formed in a portion of the rigid outer shell 940 of the ear protector 120 and a mounting member 910 having a ball portion adapted to be retained in the socket 950 and an arm attachment portion adapted to engage with the arm. The arm attachment portion is retained in a slot in the arm, in the cross section illustrated in FIG. 9b, shows the mounting member 910 being retained between two portions 930, 930' of the arm. It should be appreciated that the ball and socket joint enables the ear protector 920 to be moved freely through a range of angles and also enables rotation of the ear protector about the mounting member 910. The mounting member may also be formed to enable rotation of the arm around the mounting member 910, for example if the section of the mounting member retained in the slot has a circular cross section or narrow enough cross section to facilitate rotation in the slot. Alternatively the mounting member may be shaped such that the arm cannot rotate about the mounting member, rather the mounting member and arm remain in fixed orientation and only the ear protector rotates about the mounting member. In an alternative embodiment the mounting may be configured to enable rotation of the arm about the mounting but the ear protector may be prevented form rotational movement about the mounting and adapted for angular adjustment relative to the mounting only. This embodiment still enables relative rotation of the arm and ear protector.

It should be appreciated that many mounting variations are possible to enable relative rotation of the arm and ear protector and any such variation is envisage for embodiment of the eye and ear protection apparatus. For example, a ball and socket joint or hinge may be used for an arm mounting enabling the ear protector to be rotated outwardly from the wearer's head or "flipped" up to expose the ear. The mounting may be varied depending on the construction of the ear protectors, for example where the ear protector does not have a rigid outer shell, such as an ear muff constructed of fabric and foam, the mounting may be attached to the ear muff by gluing or sewing which allows angular movement but not rotation of the ear muff relative to the mounting, and the mounting may be retained on the arm in a manner which enables rotation of the arm relative to the mounting, such as a button in a slot.

A second embodiment of an ear and eye protection apparatus is illustrated being worn by a person in FIGS. 12 to 15b. The eye and ear protection apparatus 1200 comprises an eye protector 1210 adapted to form a barrier for protecting a wearer's eyes, and two ear muff style ear protectors 1220, 1225. Two arms 1230, 1235 are each connected to one side of the eye protector 1210 and an ear protector 1220, 1225 is connected to each arm 1230, 1235 respectively using a mounting 1250, 1255 located towards an upper edge of the ear protector. The assembly of the arms 1230, 1235 and eye protector 1210 is resiliently formed such that, when worn, the resilience of the assembly urges the arms and respective ear protectors 1220, 1225 inwardly to grip the wearer's head 1205 and support the apparatus 1200 in place when worn.

In some embodiments the materials from which the eye protector 1210 and arms 1230 are formed is sufficient to provide the arm and eye protector assembly with sufficient resilience to force the ear protectors inwardly to securely grip the wearer's head 1205 as illustrated. However, in some embodiments the material of the arms or eye protector may not provide sufficient inherent resilience to grip the wearer's head securely. For example, a material which has the combined properties of being sufficiently transparent for use as an eye protector and sufficiently resilient may be difficult or costly to obtain.

Figure 12:
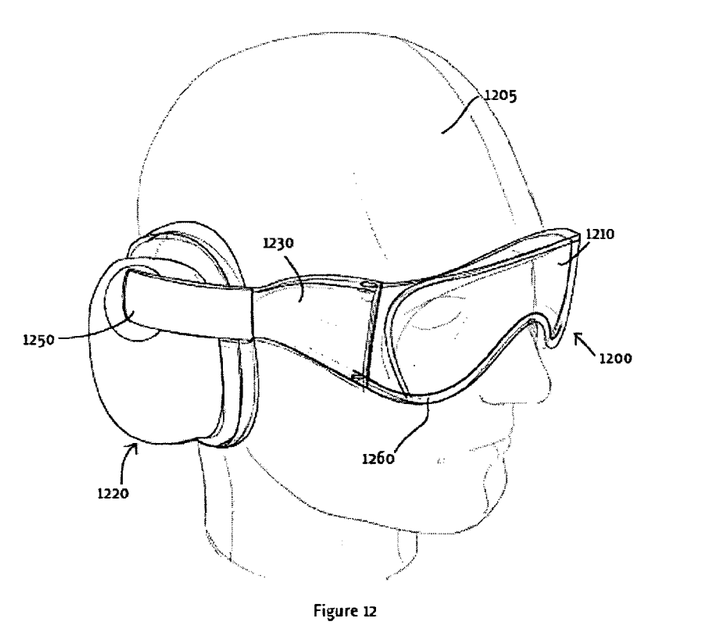
FIG. 12 illustrates a further alternative embodiment of a combined ear and eye protection apparatus.

In such embodiments an additional tensioning member 1260 may be provided to compensate for insufficient inherent resilience in the materials used. For example, as illustrated in FIG. 12, the tensioning member 1260 can be a wire extending along the lower rim of the eye protector 1210 and attached to the arms 1230, 1235. Alternatively the tensioning member may extend along the top of the eye protector. Alternatively the tensioning member may extend along both the top and bottom of the eye protector or around the eye protector like a frame. It should be appreciated that any arrangement is suitable, provided the wearer's vision is not unduly obstructed.

In the embodiment illustrated the tensioning member is a resilient wire or piece of resilient metal attached to or embedded in the eye protector rim. However, alternative materials such as plastic, fibreglass, carbon fibre, hybrid materials etc are envisaged. Any material having sufficient resilient properties may be used for the tensioning member. The arrangement of the tensioning member within the eye protector and arm assembly will vary depending on the properties of the tensioning member material. For example, the tensioning member may comprise one or more bands of tensioning member material extending directly across the eye protector if this does not adversely interfere with the optical properties of the eye protector.

The rotational attachment of the ear protector 1220 to the arm 1230 of this embodiment limits the relative movement between the arm and ear protector such that the ear protector cannot be flipped away from the wearer's ear. Wearing ear protectors "flipped" may make the apparatus more prone to dislodgement from the wearer's head and thus desirable to discourage or inhibit in some environments. Further, wearing ear protection at all times is encouraged or mandated on some sites.

In this embodiment rotational movement about the axis parallel to the length of the arms is limited to prevent the ear protectors being flipped away from the wearer's head. Rotational movement about the axis perpendicular to the arm is maintained at least sufficient to enable the eye protector to be rotated away from the wearer's eyes. This rotational movement may enable an ear protector 1220 may only be rotated to expose or cover a wearer's ear independently of the eye protector 1210 or other ear protector 1225. For example, movement similar to that illustrated in FIGS. 3 and 4 may still be possible. However, the rotational mounting may restrict relative movement to inhibit the ear protectors being moved sufficient to expose the wearer's ears. For example, movement of the eye protector may be limited to between resting on the wearer's nose and resting on the wearer's forehead above their eyebrows. This limited range of movement may be insufficient to enable the ear protectors to be moved to expose the wearer's ears. Friction in the rotational mounting can be sufficient to inhibit the eye protector from being dislodged from a resting position on the wearer's forehead.

Figure 13A:
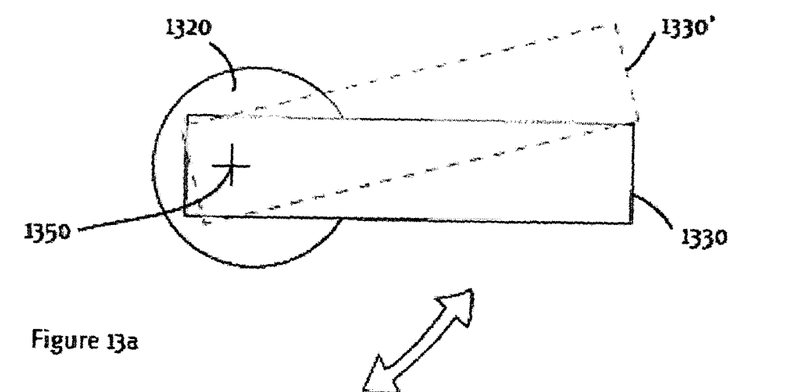
FIGS. 13a and 13b illustrate alternative arm mountings usable for embodiments of the combined eye and ear safety apparatus.
Figure 13B:
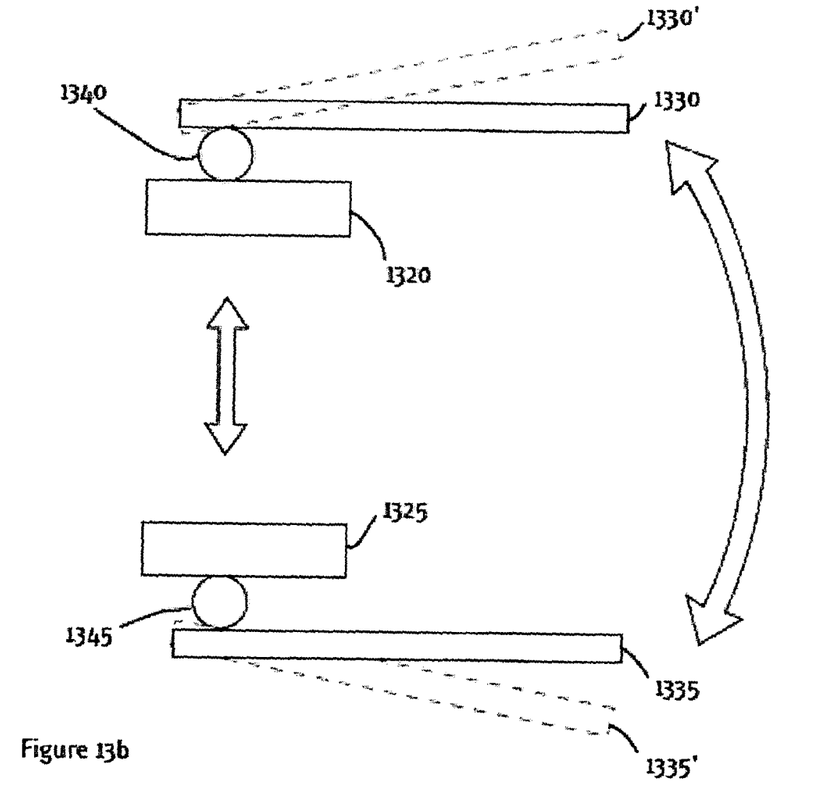
Figure 14A:
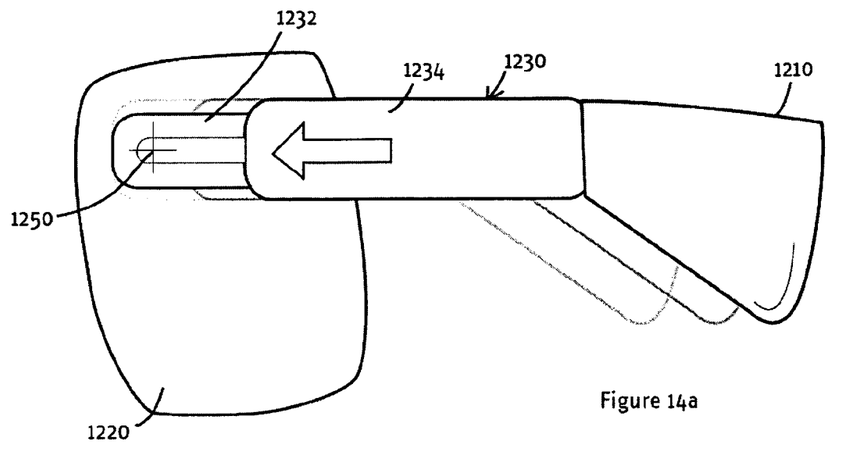
FIGS. 14a and 14b illustrate relative ear protector and arm positions enabled by some arm mounting embodiments.
Figure 14B:
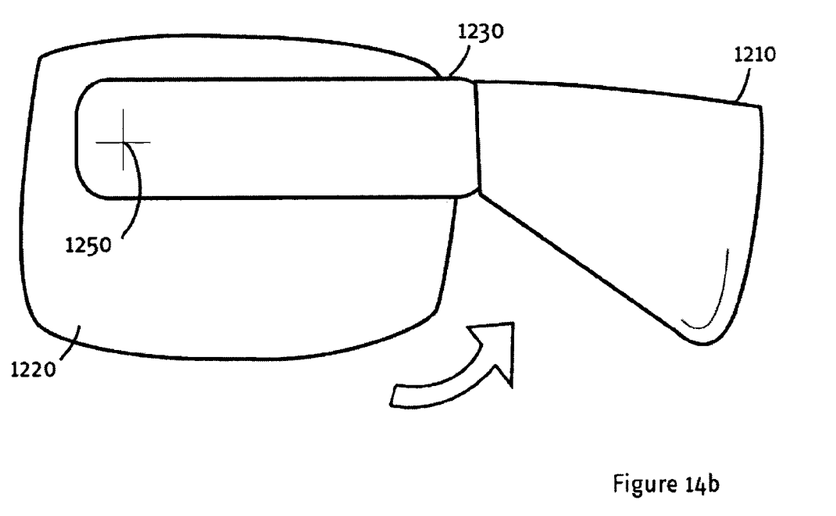

The rotational mounting 1250 of the ear protector 1220 to the arm 1230 of this embodiment can be implemented using a disc and pivot arrangement, as illustrated in FIG. 13*a*. The disc 1320 is connected to the arm 1330 by a pivot mounting 1350. This enables rotational movement of the arm 1330' about one axis. In this example the disc 1320 can be attached to the ear protector.

Where some movement may also be desired about an axis perpendicular to the arm 1330, a secondary pivot mounting maybe provided. For example, as illustrated in FIG. 13*b* a second pivot mounting 1340, 1345 may be provided between the respective arm 1330, 1335 and disc 1320, 1325. To enable some movement of the arms 1330', 1335' about the axis of the second pivot mount. The range of this movement may be limited, for example to only enable some angular adjustment of attached ear protectors. Alternatively, the movement may be limited to a range which enables the ear protectors to move between a rest and wearing position. For example, allowing the ear protectors to rest together when the safety apparatus is not being worn and be moved to a comfortable wearing position.

Each arm can also be adapted to enable the distance between the ear protector and eye protector to be adjusted. In the embodiment illustrated in FIGS. 14*a* and 14*b* the arm 1230 is in two sections 1232, 1234 which are slidingly engaged to enable the arm to be shortened or lengthened. For example, one portion of the arm 1232 may slide over the other portion 1234 and be held in place by friction between the two portions 1232, 1234 of the arm. This adjustability enables the relative positions of the ear protectors and eye protector to be adjusted to suit the wearer's face. This also enables the wearer to remove the eye protector without disturbing the ear protectors, by lifting the visor which can then rest comfortably on the wearer's head.

Figure 15A:
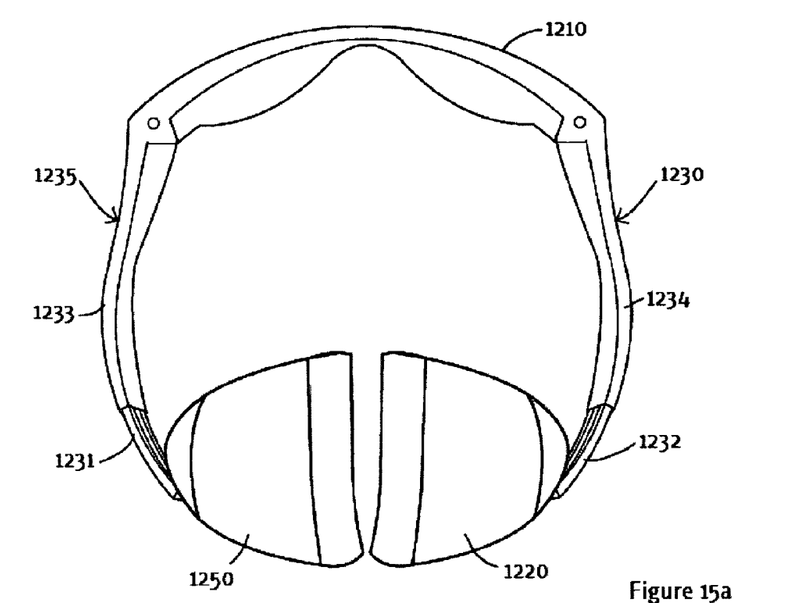
FIGS. 15a and 15b illustrate storage positions for an embodiment of the combined ear and eye protection apparatus.
Figure 15B:
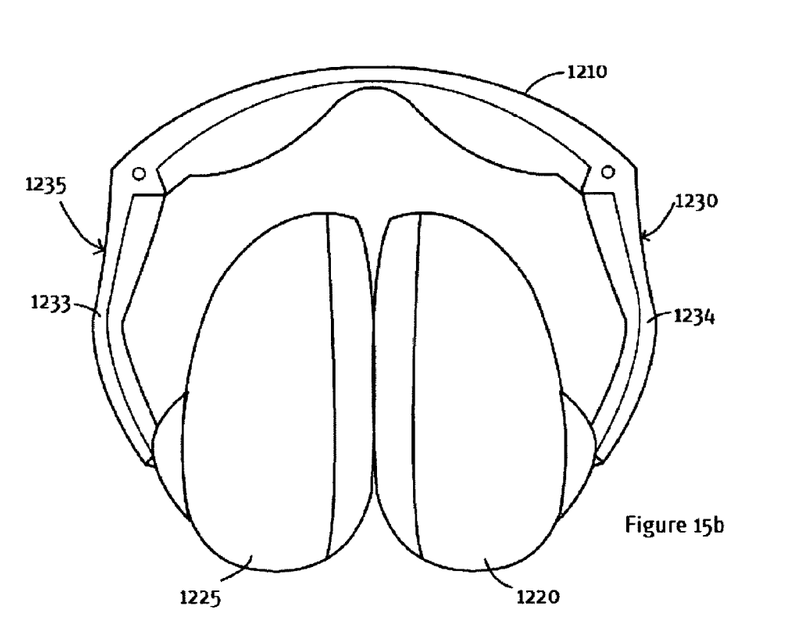

FIGS. 15*a* and 15*b* illustrate an arrangement for storage of the eye and ear protection apparatus. In this embodiment the arms do not fold for storage, rather the arms 1230, 1235 are retracted by sliding the extendable portions 1232, 1231 of the arms into the fixed portions 1234, 1233. The ear protector portions 1220, 1225 can then be rotated toward the eye protector. As can be seen in FIG. 15*b*, the ear protectors are held together to inhibit dust, dirt, debris or other contaminates accumulating in the ear muffs when they are not being worn.

In the embodiments illustrated each ear protector 120 comprises an inner sound insulating portion 122 adapted to rest against and substantially or entirely cover the outer ear of a wearer, and an outer shell 123 made of rigid material and attached to the inner insulating portion 122. The mounting 150 for connection to the arm 130 is attached to the outer shell 123 of the ear protector 120 towards the upper portion of the ear protector.

Figure 11:
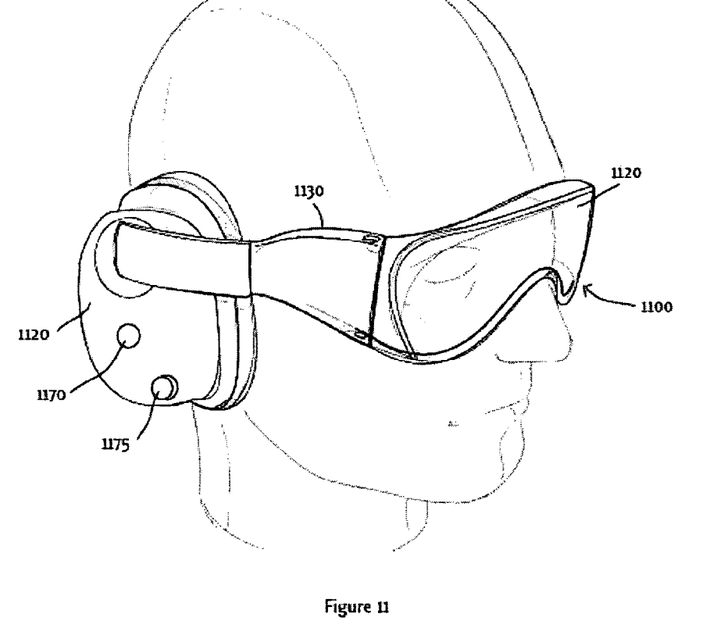
FIG. 11 illustrates a further alternative embodiment of a combined ear and eye protection apparatus.

FIGS. 4 and 6 illustrate an ear protector being moved away from a wearer's ear to enable the wearer to hear external sounds. However, in some environments any removal of ear protection is undesirable. Further moving the ear protector can be awkward at some times, for example when wearing a hard hat. To overcome this problem an ear protector which enables a wearer to selectively reduce the level of sound protection is provided. This can be provided by aperture through a portion of the ear protector which can be selectively opened by the wearer to reduce the sound protection level. As illustrated in FIG. 11 an aperture 1170 through the outer shell of the ear protector 1120 is provided. The aperture can be opened and closed by the wearer. When open, the sound protection provided by the ear protector is reduced compared to when the aperture is closed. This sound protection reduction can be sufficient to enable a wearer hear external sounds without removing all ear protection. For example to enable the wearer to answer their mobile phone, talk on a radio or hear a person talking to them.

An actuator can be provided to facilitate opening and closing of the aperture. In the embodiment illustrated a button 1175 is provided on the ear protector 1120. Pressing the button causes the aperture 1170 to open. The button can be located in a position where it can be easily pressed while a mobile phone is being held proximate the ear protector. Although a button is used in this example, alternative actuators are envisaged, for example switches, pressure pads, levers etc. The actuator may be integral to the aperture, for example the actuator may be an edge of the aperture cover, hinged such that the aperture opens when the cover edge is pressed.

In some embodiment the aperture may be normally closed and only opened while the actuator is being operated. For example, maintaining the aperture open while the button is pressed and automatically closing the aperture when the button is released. For example, the aperture may be biased to close and the actuation acts against the bias to open the aperture. Once the actuator is release the bias causes the aperture to close. The bias may be provided a resilient member such as a spring or elastic web. The bias may alternatively be magnetic. Alternatively elasticity of the outer shell material or an aperture cover may be exploited to provide the bias to close the aperture.

In an alternative embodiment the actuator can be adapted to toggle the aperture between open and closed positions. For example, a first press of the button may toggle the aperture open. A second press of the button is then needed to close the aperture. In another alternative embodiment the actuator may be adapted to toggle the aperture open and automatically close the aperture after a given period of time. This feature may minimise the risk of the aperture being left open and potential hearing damage due to reduced sound protection over a prolonged period of time.

In alternative embodiments the actuator may be provided with a sensor to detect when the aperture is no longer required to be open and automatically close the aperture. For example, this may be when a change in electromagnetic interference caused by a mobile phone transmission signal significantly reduces. This can indicate the mobile phone has been removed form the wearer's ear or the call terminated. Electromagnetic interference may also be used to trigger an automatic opening of the aperture in response to proximity of a transmitting mobile phone. Alternatively a proximity sensor may be used to detect a phone, hand, or another person talking proximate the ear protector and automatically close or open the aperture. Alternatively, a sound sensor may be adapted to respond to alteration in noise level to close the aperture, for example when it is recognised that the noise level and/or sound characteristics have returned to ambient noise.

It should be appreciated that the aperture can be sized to enable external sounds to be heard while still providing some noise protection to the wearer. Further, enabling a wearer to perform tasks such as hear a radio, mobile phone, or conversation while still wearing ear protection minimises the likelihood that the ear protection will be removed. This can have significant advantages in reducing the likelihood of hearing damage. Further combining ear and eye protection in the apparatus as described can have convenience and comfort advantages for the wearer. This in turn can improve the likelihood of using the appropriate safety apparatus.

In some embodiments the eye protector can have some vision correction properties, for example the eye protector can be configured to enable prescription lenses to be built into the device. The eye protector can also be tinted and/or polarised to provide some sun and glare protection.

It is a known problem with muff style ear protectors that the soundproofing seal between the ear protector and the wearer's head is broken when worn with safety glasses. The arm of the safety glasses pushes the ear muff away from the wearer's head, sometimes causing a significant gap. Thus reducing the sound protection provided to the wearer. This is a known problem with all ear muff style ear protectors currently available on the market. Further the ear muffs pressing safety glasses or safety goggle arm into the wearer's head can be uncomfortable. The level of discomfort can also increase over time. This, in turn, can lead to a person choosing not to wear the appropriate safety equipment to avoid discomfort. Embodiments of the present safety apparatus overcome this problem by combining ear muffs and safety glasses in a single apparatus.

In some embodiments the eye and ear protection apparatus can be configured to enable regular spectacles to be worn with the device. In some embodiments, the visor, arms and ear muffs can be configured to accommodate spectacle arms. For example the visor can be made wide enough that and the arms spaced widely enough so that spectacle frames can fit behind the visor not rub or otherwise interfere with the arms. The ear muffs can also have a slot or softer portion in the ear engaging foam near the top of the ear to minimise discomfort where the top portion of the outer ear may be pressed against the spectacle arm by the ear protector. Further, this can minimise any disruption to the sound proofing seal between the ear protector and the wearer's head caused by the spectacle arms. Alternatively the ear protector may be formed in a manner which leaves the top portion of the wearer's ear exposed so that it will not be pressed against a spectacle arm.

The ear protectors do not need to be moved to enable the wearer to hear external sounds clearly where selectively openable apertures are provided in the ear protectors. In such embodiments the ear protector may be adapted to accommodate spectacle arms. For example, a slot may be formed in foam padding around the ear protector into which a spectacle arm can be slid. Thus padding sitting against the wearer's head is not obstructed by the spectacle arms, reducing the sound protection provided. This may also improve comfort for a person needing to wear the ear protectors with spectacles. Further, the spectacle arms may be held relatively firmly in the ear protector foam, in turn holding the spectacles in place on the wearer. This may have a safety advantage as the spectacles are less likely to be dislodged or require adjustment while working. Further, this can reduce the likelihood of the wearer's spectacles being dislodged when the eye protector is moved.

A further embodiment of the safety apparatus providing ear protection only is also envisaged. For example, ear protectors selectively openable apertures may be mounted on a traditional head band style body. Embodiments may also be adapted, as described above, to be worn with regular spectacles. For example, an embodiment where the ear protectors have slots for receiving spectacle arms without disruption to the sound proofing seal. Such an embodiment may be useful for a person who wears spectacles and requires hearing protection in a situation where safety goggles are not needed. For example, while driving a tractor driver or practicing drums.

The mounting 150 position illustrated in FIG. 1 has an advantage of exposing a substantial portion of the outer shell 123 of the ear protector 120. This exposed area can be used to carry advertising, for example a logo 124 printed on the outside of the outer shell or on a sticker adhered to the outer shell.

In some embodiments the outer shell has a removable portion adapted to be selectively removed and replaced. The removable portion can be printed with information such as advertising and enable the advertising to be changed by removing and substituting an alternative removable portion bearing different advertising.

In some embodiments removing the removable portion exposes an aperture in the outer shell. In the embodiment of the eye and ear protection apparatus 1000 illustrated in FIG. 10 an ear protector 1020 has an aperture 1060 in the outer shell 1040 which is fitted with a removable portion 1050. For example the removable portion 1050 can be a snap in plate which is fits into the aperture. Removing the plate 1050 enables access to the inside of the ear protector through the aperture 1060. For example, the aperture may enable the sound insulating qualities of the ear protector to be adjusted by adding or removing additional sound insulating material. Although in the embodiment illustrated the removable portion is a snap in plate alternatives such as a screw in, hook and loop or adhesive fastenings are also considered.

Figure 10:
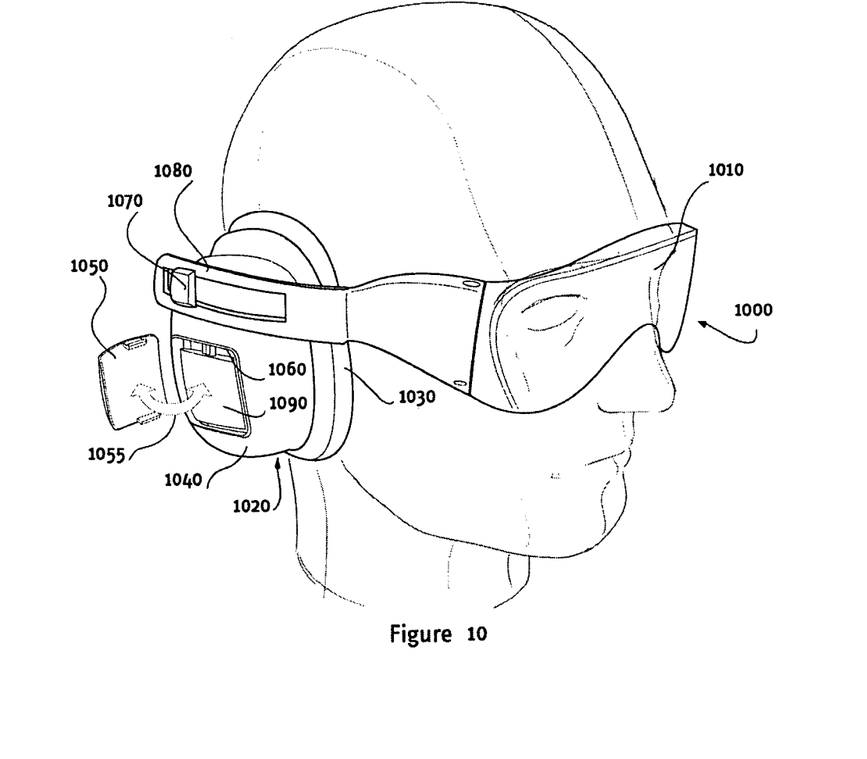
FIG. 10 illustrates an alternative embodiment of a combined ear and eye protection apparatus.

The aperture can also enable an active element 1090 to be placed inside the ear protector 1020. The active element may be a communication device, for example, an active element may be a radio receiver or wireless hands free device for a mobile phone. In some embodiments the active element may be mounted on an alternative or replacement removable portion for the ear protector. For example an ear protector may have a rigid plastic outer shell with a removable portion.

An alternative removable portion may be available for purchase which includes an active element, for example a Bluetooth hands free device for a mobile phone. The original removable portion can be removed from the ear protector and replaced with the Bluetooth alternative removable portion, which includes a microphone, speaker, Bluetooth transceiver and optional controls such as a volume control and answer button. The Bluetooth device can be wirelessly connected to the wearer's mobile phone and used by the wearer when making or receiving phone calls so the ear protector does not need to be removed. The hands free device could be specifically designed for operating in a noisy environment, for example by including active noise cancelling. By providing the active element on a replacement removable portion, the active element can be purchased as an optional accessory to the eye and ear protection apparatus and replaced or removed as desired.

Alternative removable portions could be provided having a variety of different active elements. Active elements may be provided for communication purposes, such as radio receivers, transceivers or mobile phone hands free devices. Other active elements may be provided for entertainment purposes, such as music players or FM radio receivers.

Alternatively active elements may be provided for safety monitoring. For example, an active element such as a decibel monitor may be used to track exposure of the wearer to noise. For example, this information may be used to alert the wearer, a supervisor, safety auditor or manager to noise events above a given threshold or to prolonged exposure above a given threshold noise level. Another active element may be a sound recorder which may be used for monitoring activities, types of noise or for investigation in the case of an accident. Other safety monitoring devices may be unrelated to sound, such as temperature monitoring or GPS positioning. It should be appreciated that a variety of safety monitoring devices could be provided and having these on replaceable plates enables the devices to be changed according to the work environment or monitoring activity being performed.

An alternative embodiment may be provided for ear protections only. For example, ear muff style ear protector device having a body for permitting positioning on a wearer's head, and two ear muff ear protectors connected with the body, so the ear protectors can be operatively held relative to a wearer's ears so that one ear protector can cover one ear and the other ear protector can cover the other ear. Each ear protector is connected with the body by a swing coupling such that an ear protector can be swung from about the swing coupling to crank the ear protector so that the wearer's ear is no longer covered whilst leaving the body positioned on the wearer's head. The direction of swinging can be fore/aft of the wearer's head along the side of the wearer's head. Alternatively the direction of swinging can be laterally outwardly/inwardly of the wearer's head. Each swing coupling can have an axis of swing rotation positioned in an upper region of an ear protector. It should be appreciated that this embodiment may be worn with conventional safety goggles or eyewear such as spectacles or sunglasses.

In an alternative embodiment, an eye and ear protection apparatus can be provided having a an eye protector and two ear muff style ear protectors mounted on resilient arms removably connected to respective sides of the eye protector such that, when worn, the resilience of the arms urges the arms and respective ear protectors inwardly to grip the wearer's head and support the apparatus in place when worn. In this embodiment, the arms are removable to enable the arms and their respective ear protectors to be removed and replaced with arms adapted to rest behind the wearer's ears such that the ear and eye protection apparatus can be converted to an eye protection device only.

For example, where a user has gone to additional expense to have the eye protection made with vision correction, it may be desirable to be able to convert the apparatus between a combined ear and eye protection apparatus and an eye protection only apparatus. Any suitable fastener may be used to make the arms removable. For example the arms may use releasable hinges. Alternatively a portion of the arms may be removable, for example the end portion of the arms which curves outwardly to accommodate the ear protectors may be removably attached to a front portion of the arm which is connected to the eye protector. For example, the end arm portion may be retained in a cooperatively shaped slot or cavity in the front portion of the arm, and held in engagement by friction or a releasable fastener. The end portion of the arms, with their respective ear protectors, may be removed and replace with arm portions adapted extend directly back to hook behind the wearer's ear.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

The invention claimed is:

1. An ear muff style ear protector device comprising:
a body for permitting positioning on a wearer's head;
two ear muff ear protectors connected with the body, so the ear protectors can be operatively held relative to a wearer's ears so that one ear muff ear protector can cover one ear and the other ear protector can cover the other ear; and no headband;
at least one ear protector being adapted to selectively enable the wearer to temporarily reduce the level of sound protection to the respective ear to enable external sounds to be heard more clearly;
the body being an eye protector assembly which is connected to each one of the two ear muff ear protectors via a rotational mounting, each ear muff ear protector having a center equidistant from all edges, wherein the rotational mounting is located closer to an upper edge of the ear muff ear protector than the center of the ear protector, so that when worn each connection between the ear protector and eye protector assembly will be positioned relative to the wearer's ear, and the body can be rotationally moved independently of the ear protectors between a first position where the body rests on the wearer's face to provide protection to the wearer's eyes and one or more alternative positions where the body rests in a position where protection is not provided to the wearer's eyes while the ear protectors can be operatively held relative to a wearer's ears so that one ear protector can cover or uncover one ear and the other ear protector can cover or uncover the other ear;
the eye protector assembly being resiliently formed such that the resilience of the eye protector assembly applies force to the ear protectors toward an upper edge of each ear protector to urge the respective ear protectors inwardly to grip the wearer's head and support the device in place when worn; and
each rotational mounting having a member rotationally connecting the eye protector assembly to the ear protector and providing an axis of rotation for relative rotational movement between the ear protector and eye protector assembly located closer to the upper edge of the ear protector than the center of the ear protector, allowing pivoting of the ear protector around the axis of rotation to result in the lower edge of the ear protector swinging in an arc to uncover the wearer's ear without requiring movement of the eye protector while the apparatus/device is held in place on the wearer's head solely by pressure applied to the ear protectors through the rotational mountings by resilience of the eye protector assembly.

2. An ear muff style ear protector device as in claim 1, wherein each ear protector is connected with the body by a swing coupling such that an ear protector can be swung from about the swing coupling to crank the ear protector so that the wearer's ear is no longer covered whilst leaving the body positioned on the wearer's head.

3. An ear muff style of ear protector device as in claim 1, wherein at least one ear protector is provided with an aperture in a portion of the ear protector wherein the aperture can be selectively opened by the wearer to temporarily reduce the level of sound protection provided from the level of sound protection provided while the aperture is closed.

4. A combined ear and eye protection apparatus comprising:
- an eye protector assembly including an eye protector adapted to form a barrier for protecting a wearer's eyes, and arms connected to the eye protector for permitting positioning on a wearer's head;
- two ear muff style ear protectors each having a rotational mounting, each ear muff ear protector having a center equidistant from all edges, wherein the rotational mounting is located closer to an upper edge of the ear muff ear protector than the center of the ear protector and attached to one of the arms, so that when worn the mounting will be positioned relative to the wearer's ear toward the top or above the wearer's ear; and no headband;
- the assembly of the arms and eye protector being resiliently formed such that, when worn, the resilience of the assembly urges the arms and respective ear protectors inwardly to grip the wearer's head and support the apparatus in place when worn so the ear protectors can be operatively held relative to a wearer's ears so that one ear protector can cover one ear and the other ear protector can cover the other ear, and each rotational mounting having a member rotationally connecting the eye protector assembly to the ear protector and allowing pivoting of the ear protector to result in the lower edge of the ear protector swinging in an arc to uncover the wearer's ear without requiring movement of the eye protector while the apparatus is held in place on the wearer's head.

5. A combined ear and eye protection apparatus as in claim 4, wherein at least one ear protector is adapted to selectively enable the wearer to temporarily reduce the level of sound protection to the respective ear to enable external sounds to be heard more clearly.

6. A combined ear and eye protection apparatus as in claim 5, wherein at least one ear protector is provided with an aperture in a portion of the ear protector wherein the aperture can be selectively opened by the wearer to temporarily reduce the level of sound protection provided from the level of sound protection provided while the aperture is closed.

7. A combined ear and eye protection apparatus as in claim 6, wherein the aperture is normally closed.

8. A combined ear and eye protection apparatus as in claim 7, wherein an actuator is provided which is operable by the wearer to open the aperture when actuated.

9. An ear and eye protection apparatus as in claim 5, wherein each ear protector mounting is adapted to enable the ear protector to rotate about more than one axis relative to the arm.

10. An ear and eye protection apparatus as in claim 4, wherein each arm is adapted to enable the position of the ear protector to be moved relative to the eye protector.

11. An ear and eye protection apparatus as in claim 4, wherein the mounting is a disc and pivot type joint, comprising a disc connected to the ear protector and a pivot mounting member adapted to engage with the arm to attach the ear protector to the arm.

12. An ear and eye protection apparatus as in claim 4, wherein the eye protector assembly includes a tensioning member adapted to provide sufficient resilient force to maintain grip on the wearer's head and support the apparatus in place when worn.

13. An ear and eye protection apparatus as in claim 4, wherein the materials from which the eye protector assembly is formed provide sufficient resilient force through the arms to maintain grip on the wearer's head and support the apparatus in place when worn.

14. An ear and eye protection apparatus as in claim 4, wherein each ear protector comprises:
- an inner sound insulating portion adapted to rest against and substantially or entirely cover the outer ear of a wearer; and
- an outer shell made of rigid material and attached to the inner insulating portion;
- wherein the mounting for connection to the arm is attached to the outer shell of the ear protector; and
- wherein the outer shell has a removable portion adapted to be selectively removed and replaced whereby when removed an aperture is formed in the outer shell.

15. An ear and eye protection apparatus as in claim 14, wherein sound insulating qualities of the ear protector can be adjusted by adding or removing additional sound insulating material via the aperture in the outer shell.

16. An ear and eye protection apparatus as in claim 14, wherein the removable portion of the outer shell is replaceable with an alternative removable portion adapted to substitute for the removable portion of the outer shell to fill the aperture in the outer shell.

17. An ear and eye protection apparatus as in claim 16, wherein the alternative removable portion caries an electronic device for installation in the ear protector.

18. An ear and eye protection apparatus as in claim 17, wherein the electronic device is a communication device.

19. An ear and eye protection apparatus as in claim 17, wherein the electronic device is a wireless hands free unit for a mobile phone.

* * * * *